United States Patent
Graczyk

[11] Patent Number: 6,149,661
[45] Date of Patent: Nov. 21, 2000

[54] STEP KNIFE

[76] Inventor: Paul M. Graczyk, 61 Brookside Dr., Glendale Heights, Ill. 60139

[21] Appl. No.: 09/378,144

[22] Filed: Aug. 20, 1999

[51] Int. Cl.⁷ ..................................................... A61B 17/32
[52] U.S. Cl. ........................................... 606/166; 606/167
[58] Field of Search .................................... 606/166, 167; 30/293, 294, 353, 357

[56]  References Cited

U.S. PATENT DOCUMENTS

| | | |
|---|---|---|
| 1,778,773 | 10/1930 | Reynolds . |
| 4,491,132 | 1/1985 | Aikins . |
| 4,593,133 | 6/1986 | Schmidt . |
| 5,201,747 | 4/1993 | Mastel . |
| 5,336,236 | 8/1994 | Nevyas-Wallace . |
| 5,391,177 | 2/1995 | Schwartz . |
| 5,423,840 | 6/1995 | Casebeer . |
| 5,458,610 | 10/1995 | Feaster ..................................... 606/166 |
| 5,571,124 | 11/1996 | Zelman ..................................... 606/166 |
| 5,620,453 | 4/1997 | Nallakrishnan . |
| 5,662,668 | 9/1997 | Kurwa . |
| 5,690,658 | 11/1997 | McAdams . |

FOREIGN PATENT DOCUMENTS 2010558  4/1994  Russian Federation ............... 606/166

Primary Examiner—Michael Buiz
Assistant Examiner—William Lewis
Attorney, Agent, or Firm—Robert L. Marsh

[57] ABSTRACT

A step knife for use in eye surgery has a blade which extends a predetermined length beyond a footplate. The blade has a sharpened lower edge and each of the sides have a sharpened portion near the lower edge and an unsharpened portion near the footplate.

6 Claims, 2 Drawing Sheets

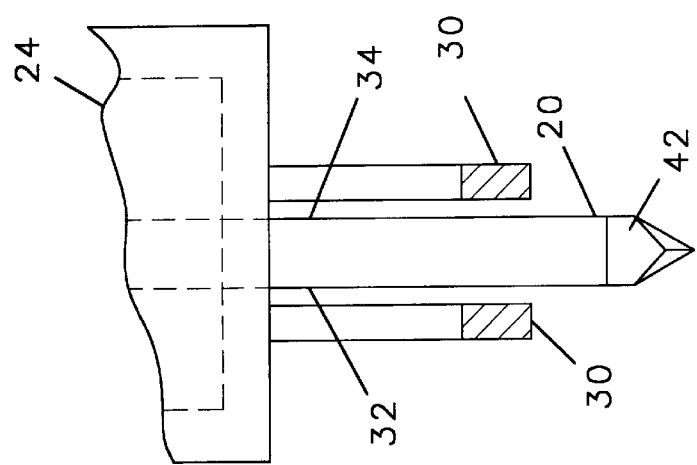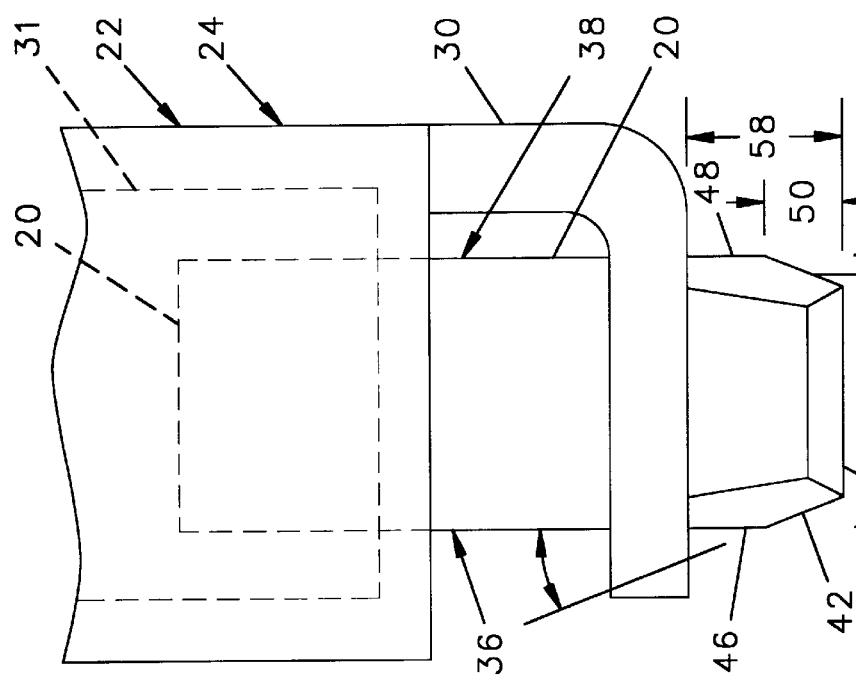

STEP KNIFE

The present application relates to eye surgery for correcting myopia hyperopia and presbiopia and in particular to a step knife for facilitating the insertion of a device such as a ring into the stroma of the cornea of an eye to facilitate the correction of such conditions.

BACKGROUND OF THE INVENTION

Surgery can be used to reshape the cornea of the eye to correct for myopia, hyperopia and presbiopia. One method of correcting for such conditions is to use a laser to reshape the surface of the cornea to change the focal length of the lens and thereby compensate for the effects of myopia and hyperopia.

In another procedure, the contour of the surface of the eye can be changed by the insertion of a ring in the stroma of the cornea. The diameter of the ring is thereafter adjusted such that the ring applies pressure to cause the cornea to become flatter and thereby compensate for myopia, or to become more curved and thereby compensate for hyperopia. This procedure is discussed at length in Kilmer, U.S. Pat. No. 5,505,722, dated Apr. 9, 1996. Kilmer discloses a ring which is inserted within the stroma of the cornea of the eye using a cutting tool configured as a coil. The cutting tool is inserted into the cornea of the eye through one or more incisions formed by a marking and cutting tool disclosed by Kilmar.

The annular insert disclosed by Kilmer must be installed through an incision in the surface of the eye. Presently, the installation is made by use of a device of the type disclosed in the Kilmer reference. The device includes a knife having an elongate blade with sharpened edges on the opposing sides of the blade.

It has been found that a problem occurs when an existing knife is used in making the initial cut prior to the installing of such a ring. Specifically, when a patient makes an eye movement just as the surgeon is plunging the blade downward through the cornea of the eye, the movement of the eye causes an excessively long installation cut. The usual consequence of this problem is that the surgery is aborted. It would, therefore, be desirable to provide a knife useable for making the installation cut required for inserting a deforming ring in accordance with Kilmer, U.S. Pat. No. 5,505,722, which will not cause the cut to be enlarged as the result of movement of the eye of a patient.

SUMMARY OF THE INVENTION

Briefly, the present is embodied in a calibrated pocket step knife for use in eye surgery having an elongate handle and an elongate blade which is fixed to a handle or is retractable within the handle. In accordance with the invention, the knife has a footplate for butting against the surface of the eye into which the blade is inserted to prevent insertion of the blade beyond a predetermined depth.

The blade has opposing planar, substantially rectangular faces, substantially parallel opposing sides, and a sharpened bottom edge. The opposing sides of the blade have sharpened portions adjacent to the bottom edge, and an unsharpened portion between the sharpened portions and the foot. In the preferred embodiment, the blade is made of diamond although several other materials are suitable for such use.

BRIEF DESCRIPTION OF THE DRAWINGS

A better understanding of the invention will be had after reading the following detailed description taken in conjunction with the drawings wherein:

FIG. 4 is a fragmentary enlarged front elevational view of the knife shown in FIG. 3;

FIG. 5 is a view of the knife and blade shown in FIG. 4 rotated ninety degrees about a vertical axis; and FIG. 6 is a front elevational view of a knife in accordance with a second embodiment of the invention,

DETAILED DESCRIPTION OF THE DRAWINGS

Figure 2:
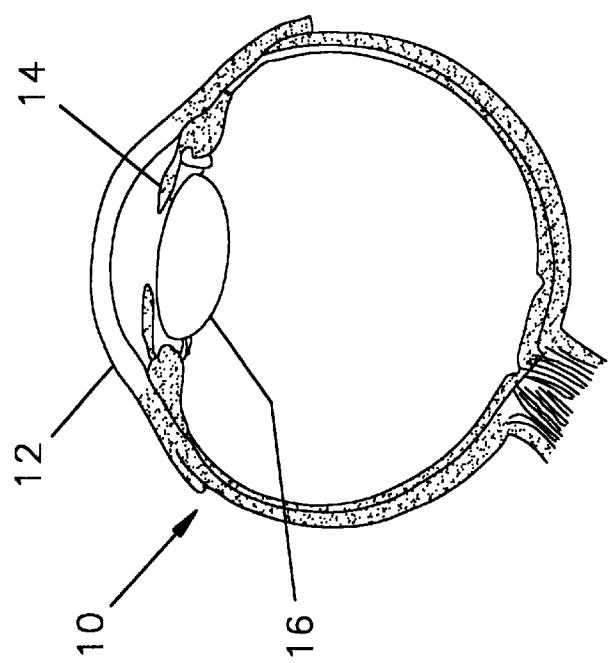
FIG. 2 is a cross sectional view of an eye into which a blade in accordance with the present invention has been inserted to facilitate the installation of the ring shown in FIG. 1.

Referring to FIG. 2, the human eye 10 includes a transparent cornea 12 behind which is an adjustable iris 14. Behind the iris 14 is a lens 16. The cells on the outer surface of the cornea comprise an epitheluim, and below the epitheluim is the stroma.

Figure 1:
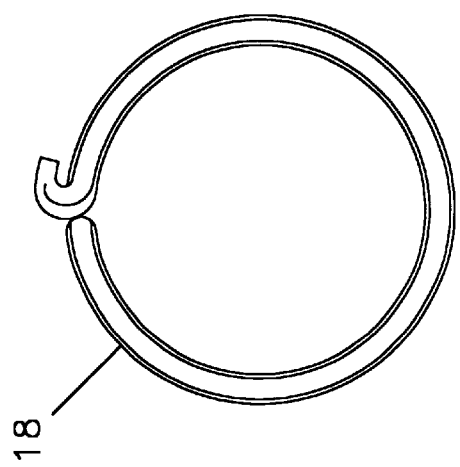
FIG. 1 is a top elevational view of a ring for insertion into the stroma of the eye to deform the surface of the eye to compensate for myopia or hyperopia.

To alter the focal length of the eye 10 a ring 18 as shown in FIG. 1 is inserted into the stroma of the cornea 12 of the eye 10. To install the ring 18 into the eye 10, an incision is made in the eye by a blade 20 in accordance with the present invention. Once the blade 20 has made a cut suitable to install the ring, the ring is installed using a device such as disclosed in Kilmer, U.S. Pat. No. 5,505,722.

Figure 3:
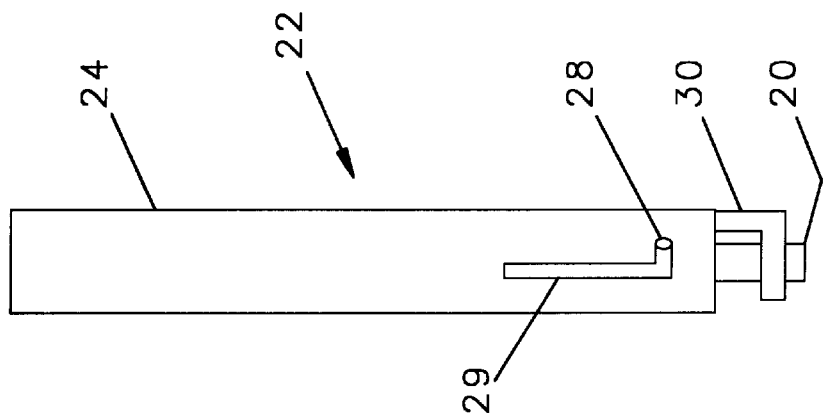
FIG. 3 is a front elevational view of the knife in accordance with the present invention with the blade extended.

Referring to FIGS. 3–5, a cut into the eye to facilitate the insertion of the ring 18 is made using a knife 22 having an elongate handle 24. The blade 20 of the knife extends axially outward of one end of the handle 24 and is moveable from a retracted position in which the blade 20 is entirely withdrawn within the handle 24, to an extended position in which the blade 20 is extended from the handle 24 as shown in the FIG. 3. A control pin, 28 extending through a slot 29 in the handle 24 insures the precision movement of the blade 20 from the extended position to the retracted position. When the blade 20 is extended, the pin 28 can be moved to a locked position, as shown, in which the blade 20 is locked with a fixed extension beyond a footplate 30. Accordingly, the footplate 30 will engage the surface of the cornea 12 of the eye when the blade 20 is inserted therein a fixed distance, such that blade 20 can be plunged to the fixed depth and no further.

For the purposes of this discussion the knife 22 and blade 20 will be described as being oriented as shown in FIGS. 3 to 5. The handle, therefore, extends upwardly and the blade extends downwardly. As shown in FIGS. 4 and 5, the upper end of the blade 20 is axially retained in a stem 31 which is moveable within the handle 20.

The blade 20 has two opposing, generally rectangular faces 32, 34 which define parallel opposing sides 36, 38. The bottom 40 of the blade 20 is sharpened to cut tissue such that the blade 20 can be plunged through the cornea until the foot 30 contacts the upper surface of the cornea 12.

In accordance with the preferred embodiment, the parallel sides 36, 38 each have sharpened portions 42, 44 respectively adjacent to the bottom 40 to facilitate plunging the blade to the desired depth. Above the sharpened portions 42, 44 are unsharpened portions 46, 48 respectively. As can be seen, the sharpened portions 42, 44 have a cutting length 50 of from 50 to 300 microns. Also, the sharpened portions 42, 44 are not perpendicular to the bottom 40, but extend from the bottom at an angle 52 of approximately eight degrees. Preferably, the blade has an overall length 54 of from 0.50 millimeters to 2.0 millimeters and has a thickness 56 of about 80 to 150 microns.

The distance 58 that the blade 20 extends below the footplate 30 defines the depth of the cut that the blade will make, and this distance is precisely fixed for each knife 22. The distance 58 may range from a minimum of 1 micron to a maximum of about 600 microns, and is chosen by the surgeon as the depth at which the ring 18 is to be inserted.

An important feature of the present invention is that movement of the patients eye while the blade 20 of the knife 22 is extending into the cornea will not result in an enlargement of the cut. This is because the unsharpened portions 46, 48 will not cut adjacent tissues.

Referring to FIG. 6, in a second disposable embodiment, a knife 60 has a blade 62 which extends a fixed length 64 with respect to a bottomplate 66. After one use the knife 60 can be discarded rather than cleaned and reused as is the knife 22 previously described.

While the present invention has been described with respect to two embodiments, it will be appreciated that many modifications and variations may be made without departing from the true spirit and scope of the invention. It is therefore the intent of the following claims to cover all such modifications and variations which come within the true spirit and scope of the invention.

What is claimed:

1. A step knife comprising a blade having opposing faces, opposing sides, and a sharpened bottom, a footplate fixing the extension of said blade from said footplate to said bottom, said opposing sides each having a sharpened portion adjacent to said bottom and an unsharpened portion between said sharpened portion and said footplate, said unsharpened portions preventing an unintentional lengthening of a cut made by said blade wherein said cut is made by plunging said blade into tissue until said footplate contacts a surface of said tissue.

2. The step knife of claim 1 and further comprising a handle adjoining an upper end of said blade.

3. The step knife of claim 1 wherein said opposing sides are substantially parallel to each other.

4. The step knife of claim 1 wherein said opposing faces are substantially parallel to each other.

5. The step knife of claim 1 wherein said sharpened portions of said sides are substantially equal in length.

6. The step knife of claim 2 wherein said blade is retractable within said handle.

* * * * *